US006322981B1

(12) United States Patent
Rodgers et al.

(10) Patent No.: US 6,322,981 B1
(45) Date of Patent: Nov. 27, 2001

(54) RAPID METHOD FOR DIAGNOSING THE VARIOUS FORMS OF ALPHA-THALASSEMIA

(75) Inventors: Griffin P. Rodgers, Kensington; Delia C. Tang, Bethesda, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/308,796

(22) PCT Filed: Nov. 18, 1997

(86) PCT No.: PCT/US97/21346

§ 371 Date: Jul. 16, 1999

§ 102(e) Date: Jul. 16, 1999

(87) PCT Pub. No.: WO98/23778

PCT Pub. Date: Jun. 4, 1998

Related U.S. Application Data

(60) Provisional application No. 60/031,880, filed on Nov. 27, 1996.

(51) Int. Cl.[7] .............................. C12Q 1/68; C12P 19/34; C07H 21/04

(52) U.S. Cl. ............................ 435/6; 435/91.2; 435/91.5; 536/23.5; 536/24.31; 536/24.33

(58) Field of Search ............................ 435/6, 91.2, 91.5; 536/23.5, 24.31, 24.33

(56) References Cited

U.S. PATENT DOCUMENTS 5,334,499 * 8/1994 Burdick et al. .......................... 435/6

FOREIGN PATENT DOCUMENTS 97 16568 5/1997 (WO) .

OTHER PUBLICATIONS

Lebo, R.V. et al. Hum. Genet. 85:293–299, 1990.*

Kropp, G.L. et al. Blood 73(7):1987–1992, May 1989.*

Newton, C.R., in PCR Essential Data, ed. C.R. Newton, John Wiley & Sons, Chichester, 1995, p. 49–56.*

Gu, Y. et al. Hum. Genet. 79:68–72, 1988.*

Kropp, G.L. et al. Blood 78(1):26–29, Jul. 1991.*

Ko, T–M. et al. J. Formos. Med. Assoc. 92(1):88–90, 1993.*

Molchanova, T.P. et al. Brit. J. Haematol. 88:300–306, 1994.*

Bowie, L.J. et al. (1994) "Detection of α–Thalassemias by multiplex polymerase chain reaction" *Clin. Chem.* 40 (12):2260–2266.

Wen, X–J. et al., (1992) "The nondeletional types of HB H disease in Guangxi" *Hemoglobin* 16(1&2): 45–50.

Liu, T–C. et al. (1994) "Molecular basis and hematological characterization of Hb G disease in southeast asia" *Am. J. of Hematology* 45: 293–297.

Orkin, S.H. et al. (1981) "Mutation in an intervening sequence splice junction in man" Proc. Natl. Acad. Sci. USA 78 (8): 5041–5405.

Bowden, D.K. et al. (1992) "A PCR–based strategy to detect the common severe determinants of α thalassaemia" Brit. J. Haematolgy 81: 104–108.

* cited by examiner

*Primary Examiner*—Carla J. Myers
*Assistant Examiner*—Diana Johannsen
(74) *Attorney, Agent, or Firm*—Morgan & Finnegan, L.L.P.; William S. Feiler; Dorothy R. Auth

(57) ABSTRACT

The present invention relates to the simultaneous and specific identification of the variant forms of α-thalassemia. This invention utilizes simple and readily available equipment to rapidly identify, diagnose and differentiate the different forms of α-thalassemia. Specifically, the present invention relates to a simple and rapid non-radioisotopic technique for the diagnosis and differentiation of the common forms of α-thalassemia has been developed. This approach works on any biological tissue including blood, wherein the assay works equally well with fresh blood and dried blood samples stored on filter paper.

9 Claims, 7 Drawing Sheets

CO-AMPLIFICATION OF $\alpha_1$– AND $\alpha_2$– GLOBIN GENES IN DNA FROM $\alpha$ – THALASSEMIAS

RAPID METHOD FOR DIAGNOSING THE VARIOUS FORMS OF ALPHA-THALASSEMIA

The instant application is a 371 of PCT/US97/21346, filed Nov. 18, 1997, and claims benefit under 35 U.S.C. 119(e) to provisional application 60/031,880, filed Nov. 27, 1996.

FIELD OF THE INVENTION

The present invention relates to the field of diagnostic methodologies. More particularly, the invention is related to a simple, inexpensive and rapid method for detecting thalassemias and monitoring therapeutic effects on the disease.

BACKGROUND OF THE INVENTION

The α-thalassemia ("α-thal") are common genetic disorders that result from reduced synthesis of the a globin chains of fetal ($\alpha_2\gamma_2$, HbF) and adult ($\alpha_2\beta_2$, HbA) hemoglobin (Weatherall and Clegg, 1981; Higgs et al., 1989, Higgs and Weatherall, 1993). The normal human α globin gene cluster is located on the short arm of chromosome 16 (Breuning et al., 1987; Buckle et al., 1988). In α-thal syndromes, α-globin synthesis is either diminished or absent due to either deletional or non-deletional abnormalities involving the α-globin genes (Higgs et al., 1989; Higgs and Weatherall, 1993). Diploid cells have four α-chain genes (i.e., αα/αα). The severity of the hematological and clinical picture is directly proportional to the number of involved α-globin genes and thus the deletion of one, two, three, or all four of these α genes attribute to mild to complete a chain deficiencies syndromes.

The deletion of α-chain at birth results in the formation of a γ chain tetramer, Hb Bart's ($\gamma_4$). The percentage of Hb Bart's present corresponds to the degree of α chain deficiency (Cong & Shong, 1982; Liang et al., 1985; Higgs et al., 1989; Higgs and Weatherall, 1993). The α-thal-2 genotype has been found to have one of the two genes deleted, thug these heterozygotes (αα/–α) possess a mild α chain deficiency resulting from the presence of only three α chain genes and have not more than 2% Hb Bart's at birth (Higgs et al., 1989). Homozygotes (–α/–α), as well as α-thal-1 heterozygotes (αα/– –), possess moderate a chain deficiency resulting from the presence of only two α chain genes and have approximately 5% Hb Bart's at birth (Higgs and Weatherall, 1993). While Hb H disease is a heterozygosity for α-thal-2 in association with an α-thal-1 heterozygosity (– –/–α), a severe α chain deficiency occurs due to the deletion of three α chain genes (Higgs et al., 1989; Higgs and Weatherall, 1993). The α-thal-1 homozygotes (– –/– –), which lack any functional α genes, present with Hb Bart's is known as hydrops fetalis syndrome and results in intrauterine or early post-delivery death to the fetus (Lie-Injo & Hie, 1960; Higgs et al., 1989). Mother bearing fetuses with homozygous α-thal-1 (– –/– –) are at high risk for obstetrical complications, such pregnancy induced hypertension, eclampsia, and/or death.

At present, for a variety of technical, logistical and economical reasons, large-scale carrier screening and appropriate ante-natal detecting programs have not been established for the populations in which this syndrome occurs (Bowden et al., 1992; Higgs and Weatherall, 1993).

It is an object of the invention to develop a diagnostic method and kit for the detection and quantitation of hemoglobin (Hb) α gene(s) in α-thalassemia patients.

It is another object of the present invention to develop a method and kit for screening for carriers of the genetic disorder, α thalassemia.

It is yet another object of the present invention to identify persons who are at risk of having offspring with homozygous α-thalassemia as well as identify α-thalassemia in individuals with unexplained microcytosis and hypochromia.

Another object of the present invention is to develop a sensitive, non-radioisotopic test capable of differentiating between the various forms of α-thalassemia, by detecting and quantitating a gene(s) from blood samples.

SUMMARY OF THE INVENTION

The present invention relates to the identification of primers capable of detecting and distinguishing between the various forms of α-thalassemia. The α-globin primers of the present invention are derived from the α-globin genes. One such primer comprises a region common to both $\alpha_1$ and $\alpha_2$ genes. A second such primer is specific for $\alpha_2$ gene and a third primer is specific for $\alpha_1$ gene. These primers are designed to specifically hybridize to portions of the hemoglobin α genes, such that, when amplified with an inducing agent, give identifiable amplification products. The presence and amount of the products is correlated to specific forms of α-thalassemia, based upon the type of gene deletion associated with the disease.

The present invention relates to a method for identifying and differentiating among the various forms of α-thalassemia. The method of the present invention uses highly specific primers to identify and differentiate among the forms of α-thalassemia. The assay may include a nucleic acid amplification step wherein the hemoglobin a genes are simultaneously amplified and detected. In another embodiment of the present invention, a color complementation assay is used to provide a convenient, rapid, non-radioisotopic, assay system for quantitation of the α gene(s).

A kit comprising at least three primers, capable of detecting, quantitating and distinguishing α-thalassemia variants is also encompassed in the present invention.

BRIEF DESCRIPTION OF THE DRAWINGS

FIG. 4. Gel scanning data from both normal and different genotypes of α-thal syndrome patients, wherein

DETAILED DESCRIPTION OF THE INVENTION

Figure 1:
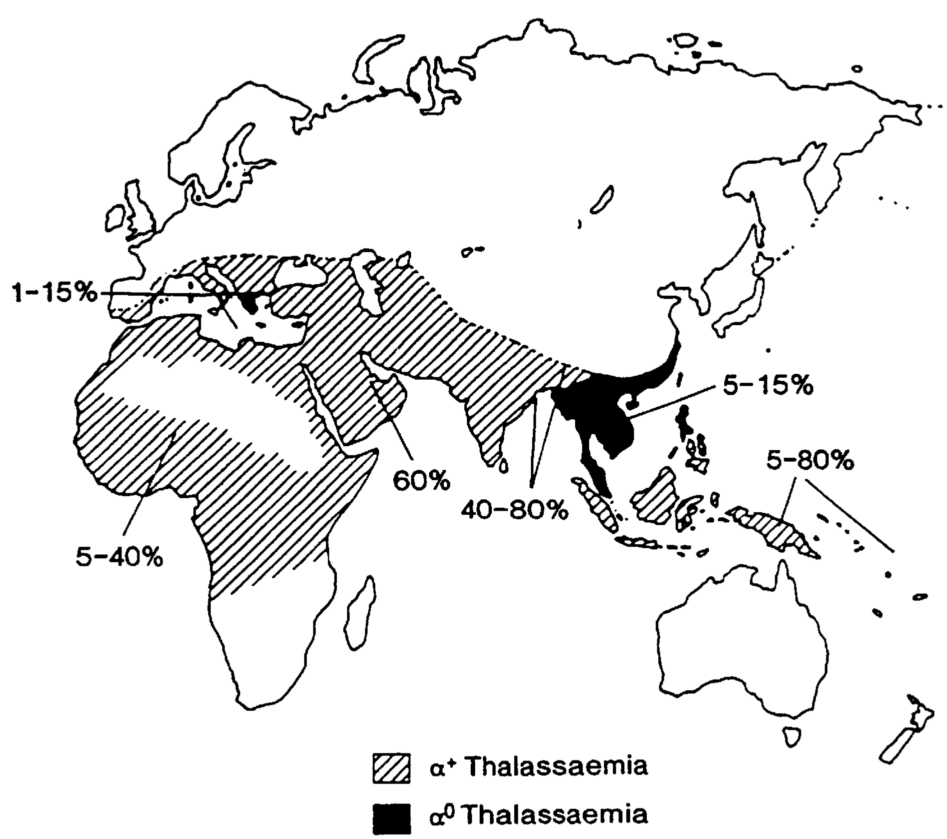
FIG. 1. Old world distribution and prevalence of α-thalassemia.

The present invention relates to the identification of nucleic acid primers capable of detecting and distinguishing between the various forms of α-thalassemia.

The primers of the present invention are used to identify and differentiate between the various forms of α-thalassemia. Samples to be tested using the present invention include blood, either dried or whole blood. In addition, samples may be derived from any biological tissue containing nucleic acid material, including but not limited to skin tissue, amniotic fluids, umbilical cord, dried tissue and paraffin embedded tissue.

A particular advantage of the present invention is its adaptability to samples in various forms; that is, the present invention can detect the various forms of α-thalassemia from fluid or dry biological samples.

The term "internal standard DNA" means a nucleic acid which will be present in a sample whether or not the target DNA is present and which can be labeled and detected independently of the globin target genes. For example, the internal standard DNA may correspond to a known sequence of DNA, i.e. a gene, on a chromosome different from that on the globin target genes.

The term "oligonucleotide" as used herein in referring to primers, probes, oligomer fragments to be detected, oligomer controls and unlabeled blocking oligomers is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, i.e. in the presence of nucleotides and an inducing agent such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. For example, for diagnostics applications, depending on the complexity of the target sequence, the oligonucleotide primer typically contains 15–25 or more nucleotides, although it may contain fewer nucleotides. For other applications, the oligonucleotide primer is typically shorter, e.g., 7–15 nucleotides.

The primers of the present invention are selected from regions of the genomic sequence of the hemoglobin α genes. The 5' primer is preferably located at the 5' end of each of $\alpha_1$ and $\alpha_2$ gene and serve as a common sense primer. Most preferred is a 5' primer comprising the sequence 5'-TGACCCTCTTCTCTGCACAGCTC-3' (SEQ ID NO: 1) corresponding to a common region in both the $\alpha_1$ and the $\alpha_2$ genes. This sequence, referred to herein as "A primer," is found at position 7242-7264 in the $\alpha_2$ gene and at position 11060-11082 in the $\alpha_1$ gene of the genomic sequence described by as set forth in Gen Bank, Accession No. J00153, also known as HUMHBA4.

Two different 3' primers provide the specificity to detect multiple a gene deletions. These primers are preferably 3' antisense sequences of the hemoglobin α genes. A preferred $\alpha_2$ 3' primer comprises a region within the 3' untranslated portion of the $\alpha_2$ gene. One such primer comprises 5'-TTCCGGGACAGAGAGAACCCAGG-3' (SEQ ID NO:3). This sequence, referred to herein as "B2 primer," is found at position 7512-7534 in the genomic sequence as set forth in Gen Bank, Accession No. HUMHBA4. A second preferred $\alpha_1$ 3' primer comprises the sequence 5'-GAGGCCCAAGGGGCAAGAAGC-3' (SEQ ID NO:2) corresponding to a region within the 3' untranslated portion of the $\alpha_1$ gene. This sequence, referred to herein as "B1 primer," is found at position 11229-11249 in the genomic sequence as set forth in Gen Bank, Accession No. HUMHBA4.

The primers of the present invention can be used in various ratios in detection of the different forms of α-thalassemia. Ratios selected will depend upon several factors, including the method of detection used, the amount of nucleic acid material and the source of the biological sample. When using amplification techniques, it is preferred that the 5' common sense primer is present at a ratio range of 1–2 and the 3' $\alpha_2$ and 3' $\alpha_1$ primers are present at a ratio range of 0.1–1.5. A particularly preferred embodiment when using amplification techniques is 5' common sense primer: 3' $\alpha_1$ primer, 3' $\alpha_2$ primer ratio of about 1:1:1.

The primers may vary in size but preferably contain a substantial portion of SEQ ID NO:1, SEQ ID NO:2, and SEQ ID NO:3. Specific nucleotide positions of the primers may be varied so long as the primers retain their ability to specifically hybridize to the hemoglobin α genes.

Primers are readily synthesized by standard techniques. Detailed procedures for the phospho-triester and hydrogen phosphonate methods of oligonucleotide synthesis are described in the following references, which are incorporated by reference: Caruthers et al., U.S. Pat. Nos. 4,458,066 and 4,500,707; Matteucci et al., *J. Amer. Chem. Soc.* 103:3185–3191 (1981); Caruthers et al., *Genet. Engin.* 4:1–17 (1987); Jones, Chapter 2 and Atkinson et al., Chapter 3, in Gait, ed., *Oligonucleotide Synthesis: A practical Approach* (IRL Press, Washington, DC, (1984); Froehler, et al., *Tetrahed. Lett.* 27:469–472 (1986); Garegg, et al., *Tetrahed. Lett.* 27:4051–4058 (1986); and Froehler, et al., *Nucl. Acid Res.* 14:5399–5407 (1986).

The primers of the present invention can be used for amplification using standard polymerase chain reaction techniques. Mullis U.S. Pat. Nos. 4,683,202 and 4,683,195 describe the basic amplification technique and are incorporated herein by reference. Other variant amplification techniques, can also be used. Such techniques are known to the skilled artisan.

Once amplified, the products can be analyzed by many techniques known in the art. For example, one technique uses physical separation of the amplification products to distinguish the products. Physical separation can be carried out by various methods, including but not limited to filtration, electrophoresis and chromatography techniques.

Detection and differentiation of the allele-specific amplification products may also be accomplished using immunocytochemistry methods relying on reagents that associate with one another with high specificity and affinity such as biotin-streptavidin, digoxigenin and others (Didenko, et al., 1996).

A further detection method would allow for high DNA through-put in the context of mass screening employs detection of alpha-globin gene(s) on the surface of a charge coupled device, currently known as a "DNA-chip" (Lamture, et al., 1994).

A preferred method of detecting the presence and amount of each of the amplified products is one that allows for the detection of more than one target DNA without the need to separate the different amplified products. For example, the primers of the present invention may be used in a color complementation assay, as described in U.S. Pat. No. 5,489,507, incorporated herein by reference. In brief, this embodiment comprises the steps of (i) simultaneously amplifying the target hemoglobin genes and one or more internal standard DNAs in a sample, (ii) providing one or more first labeling means capable of binding to the target hemoglobin genes in the sample, (iii) providing one or more second labeling means capable of binding to one or more internal standard DNAs in the sample, (iv) combining the first labeling means and the second labeling means with the sample so that the first labeling means binds to their target hemoglobin genes to form one or more labeled target hemoglobin genes and the one or more second labeling means bind to their respective internal standard DNAS to form one or more labeled internal standard DNAs, (v) separating the unbound first labeling means from the sample, and (vi) illuminating the sample with an illumination beam having a predetermined wavelength characteristic such that a distinct color signal is produced whose character depends on which of the one or more target DNAs that have been amplified. Preferably, the steps of simultaneously amplifying, providing ea first labeling means, providing one or more second labeling means, and combining are achieved by carrying out a polymerase chain reaction wherein the first labeling means comprises a pair of primers specific for the target globin genes, at least one of the primers being labeled directly or indirectly with a first color-producing or color-absorbing label, and wherein the one or more second labeling means comprise separate pairs of primers, at least one member of each pair being labeled directly or indirectly with a different second color-producing or color-absorbing label.

Color-producing labels and color-absorbing labels can be attached to primers in a variety of ways either directly or indirectly. Mathews et al (1988) provide a comprehensive list of both direct and indirect labeling means for nucleic acids. Accordingly, this reference is incorporated by reference.

Labels can be directly attached to primers via a 5' amino or thiol linking group, e.g. Connolly et al (1985) and Fung et al., U.S. Pat. No. 4,757,141. Many commercially available dyes with amino- or thiol-reactive moieties can be used as color-producing and/or color-absorbing labels. For example, the following dyes suitable for use with the invention are available: (i) thiol-reactive; 5-iodoacetaminofluorescein, fluorescein-5-maleimide, tetramethylrhodamine-5 (and-6) iodoacetamide, rhodamine X iodoacetamide, and the like, and (ii) amino-reactive; Fluorescein-5 (and-6) isothiocyanate, Texas Red, rhodamine X isothiocyanate, fluorescein-5(and-6) succinimidylcarboxylates, 7-amino-4-methylcoumarin-3-acetic acid, 5- and/or 6-succinimidylcarboxylates of rhodamine dyes, and the like, and dyes disclosed in U.S. pat. appln Ser. no. 07/138,287 filed Dec. 24, 1987.

Color-producing and/or color-absorbing labels can also be attached to primers indirectly via antibodies or via biotin and avidin or steptavidin. Means for synthesizing biotinylated primers is well known in the art (e.g. Chollet et al. 1985; Agrawal et al., 1986). Biotinylating reagents are also commercially available and hence are known and available in the art.

One or more different internal standard DNAs can be amplified with primers having the same label in order to vary the relative concentrations of the color-producing or color-absorbing labels at the time of analysis. For example, if one of the color producing labels is a fluorescent dye with low fluorescent efficiency and a given degree of brightness is required for color complementation, a number of internal standard DNAs can be labeled with the same "weak" fluorescent label to increase the labels relative concentration, and hence, its relative brightness.

Preferably, in automated embodiments of the present invention the first and second color-producing or color-absorbing means comprise pairs of amplification primers wherein the 5' nucleotidle of one primer of the pair is covalently attached to biotin and wherein the 5' nucleotide of the other primer is directly labeled with a color-producing or color-absorbing label. Preferably, color-producing labels are fluorescent labels, such as fluorescein, Texas Red, tetramethylrhodamine, dichlorodimethoxyfluoroscein, or the like. In some cases, fluorescent labels can also act as color-absorbing labels. Preferably, color-absorbing labels are used with a first labeling means and are organic indicator molecules which can be linked to an amino- or thiol-derivatized primer and whose absorption spectrum substantially overlaps both the emission spectrum of the illumination beam and labeling means. That is, preferably, the color-absorbing label is associated with the target DNA and the fluorescent label used in conjunction with a second labeling means. That is, preferably, the color-absorbing label is associated with the target DNA and the fluorescent label is associated with an internal standard DNA. If a target DNA is present and amplified the measured absorption will be high and fluorescence will be low. The reverse holds if the target DNA is not present. The presence of the target DNA is determined by the ratio of absorption to fluorescence intensity. Most preferably, fluorescent labels such as those disclosed in Khanna et al., U.S. Pat. Nos. 4,318,846; 4,439,356; and 4,481,136.

As mentioned above, for automated embodiments it is preferred that the first and second labeling means comprise pairs of primers, one with biotin attached to its 5' end and the other with a color-producing or color-absorbing label attached to its 5' end. In such an embodiment, after amplification, the reaction mixture containing the amplified chains are exposed to an avidin or streptavidin derivatized substrate, e.g. magnetic microspheres (Advanced Magnetics, Inc., Cambridge, Mass.). This allows for rapid separation of the amplified chains from the rest of the reaction mixture which, for example, may contain a preponderance of labeled primers associated with the target DNA if the target DNA is not present in the sample (and consequently not amplified). Separation is readily carried out by filtration, or if magnetic microspheres are used, by magnetic separation. The labeled strands of the amplified DNA are used, by magnetic separation. The labeled strands of the amplified DNA are separated from the biotinylated strands (and primers) by denaturation procedures, e.g. exposure to strong alkali solution (e.g. between 0.1 and 1.0 procedures, e.g. exposure to strong alkali solution (e.g. between 0.1 and 1.0 NaOH), or heat plus exposure to a solution of formamide and water. The biotinylated DNA is then removed with the substrate, and the remaining solution containing the labeled strands is illuminated by the illumination beam. Automation of the invention is readily carried out by use of a general purpose laboratory robot, such as the disclosed by Wilson et al., BioTechniques, Vol. 6, pgs., 776 (1988).

All articles and patents referred to herein are incorporated, in toto, by reference.

While the invention is described above in relation to certain specific embodiments, it will be understood that many variations are possible, and that alternative materials and reagents can be used without departing from the invention. In some cases such variations and substitutions may require some experimentation, but will only involve routine testing.

The foregoing description of the specific embodiments will so fully reveal the general nature of the invention and others can, by applying current knowledge, readily modify and/or adopt for various applications such specific embodiments without departing from the generic concept, and therefore such adaptations and modifications are intended to be comprehended within the meaning and range of equivalents of the disclosed embodiments.

EXAMPLE 1

Direct Analysis of Five Most Frequent α-thal Syndrome Genotypes (–α/αα,– –/αα.–α/–α,– –/–α and – –/– –) by PCR Amplification of DNA from 62 Patients, Blood Samples.

Direct analysis of 5 most frequent α-thal genotypes by PCR amplification of DNA samples from α-thal patients.

1). Primer Designing

Figure 2:
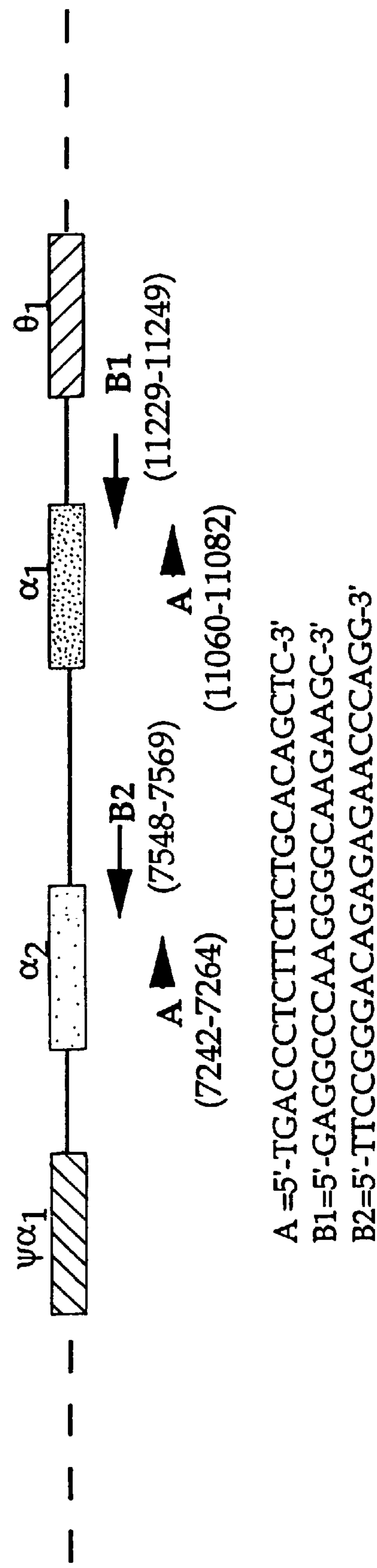
FIG. 2. Schematic representation of primers, A Primer (SEQ ID NO: 1); B1 Primer (SEQ ID NO: 2); and B2 Primer (SEQ ID NO: 3), for detecting the deletion of hemoglobin α genes.

To examine the presence of different types of α gene(s) deletion, three primers were designed for specifically coamplifying $\alpha_1$ and $\alpha_2$ genes from single blood sample by PCR. Primer $B_1$ (SEQ ID NO:2) and $B_2$ (SEQ ID NO:3) are respectively 3' antisense primer of α gene. Primer A(SEQ ID NO:1), located within the 5' portion of each $\alpha_1$ and $\alpha_2$ gene, has an identical DNA sequence for both $\alpha_1$ and $\alpha_2$ gene and serve as a common sense primer. The primers for β-actin gene (sense primer 1854 bp-1874 bp) used as an internal control. Primer design for α genes is illustrated in FIG. 2. After PCR three amplified DNA fragments: $\alpha_2$ gene (292 bp), $\alpha_1$ gene (190 bp), and β-actin gene (105 bp) could be observed from 2% NuSieve gel stained with ethidium bromide.

2). Optimal Condition for PCR Amplification

Genomic DNA (0.3 to 1 ug) is mixed with 5 μl reaction buffer, 4 μl of 125 μM dNTP, and 1 μl of each 25 μM primer (primers A, $B_1$ and $B_2$ for a genes, as well as sense and antisense primers for β-actin). The reaction is performed in 50 μl volume. The mixture is heated at 95° C. for 5 minutes to denature the DNA before 1.25 units Taq polymerase is added into the solution. Thirty cycles are performed on a Perkin-Elmer Cetus DNA thermal Cycler: denaturing at 94° C. for 1.0 min., annealing at 60° C. for 1.0 min., and extending at 72° C. for 1.0 min. After PCR reaction, 10–15 μl of the amplified product are analyzed on 2% NuSieve gel by electrophoresis. Three bands, corresponding to 190 bp for $\alpha_1$ gene, 292 bp for $\alpha_2$ gene and 105 bp for β-actin gene, were visualized. By comparing the intensity of each $\alpha_1$ or $\alpha_2$ gene bands on ethidium bromide-stained gel between normal and α-thal patient, the deletion status of α genes could be accessed.

3). Detection of α Gene Deletion from α-thal Syndrome Patients

Figure 3:
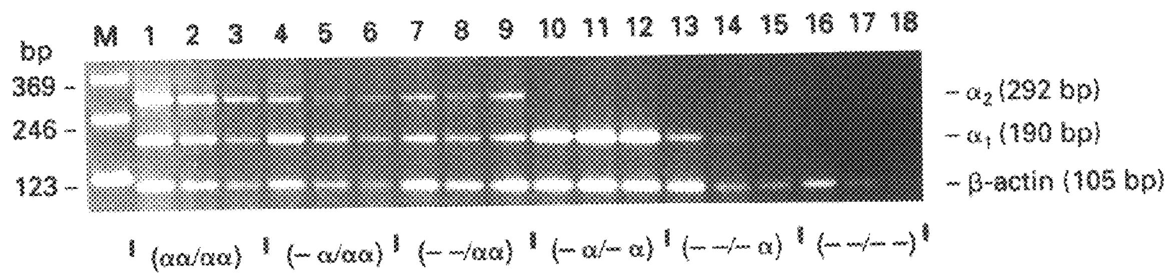
FIG. 3. Coamplification of α1- and α2-globin genes from blood samples of normal and α-thal syndrome patients. Three of each category of tested subjects are shown.
Figure 4A:
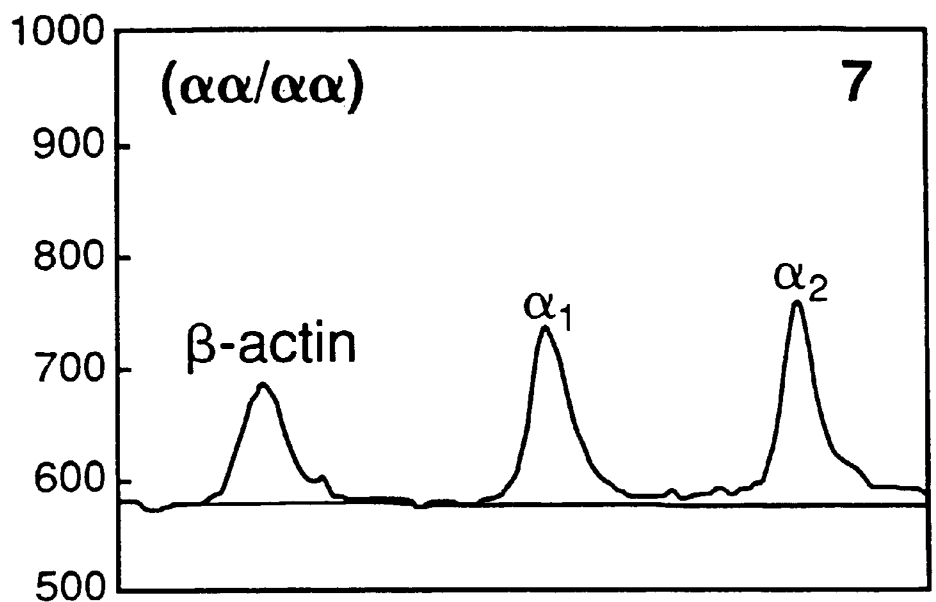
FIG. 4A represents a normal patient.
Figure 4B:
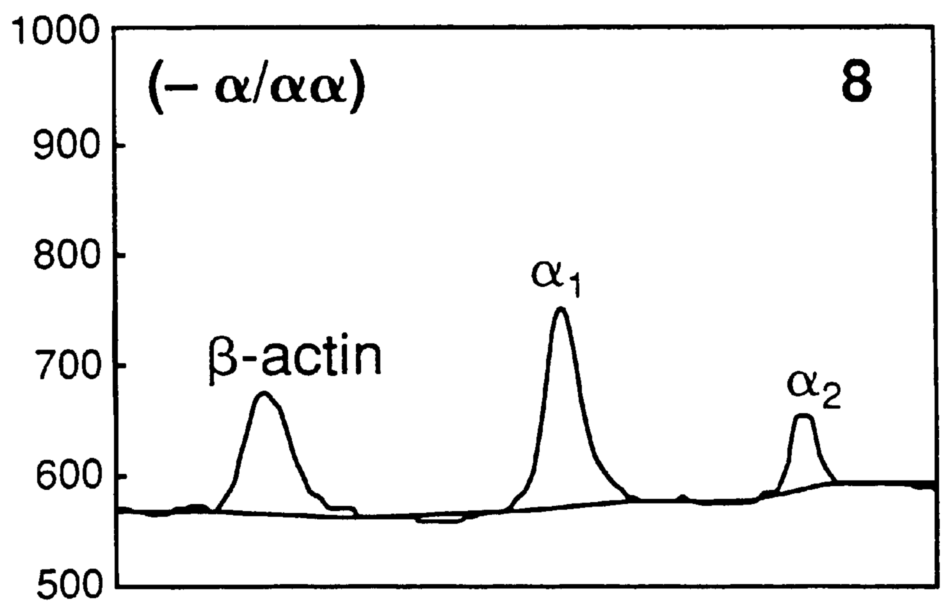
FIG. 4B represents a patient lacking an $\alpha_2$ thalassemia gene; Panels C and D represent patients with a moderate α chain deficiency, either $\alpha_1$ thalassemia heterozygous or homozygous; Panel E represents a patient with Hb H disease; and Panel F represents a patient with the Hb Bart's hydrops fetalis syndrome.
Figure 4C:
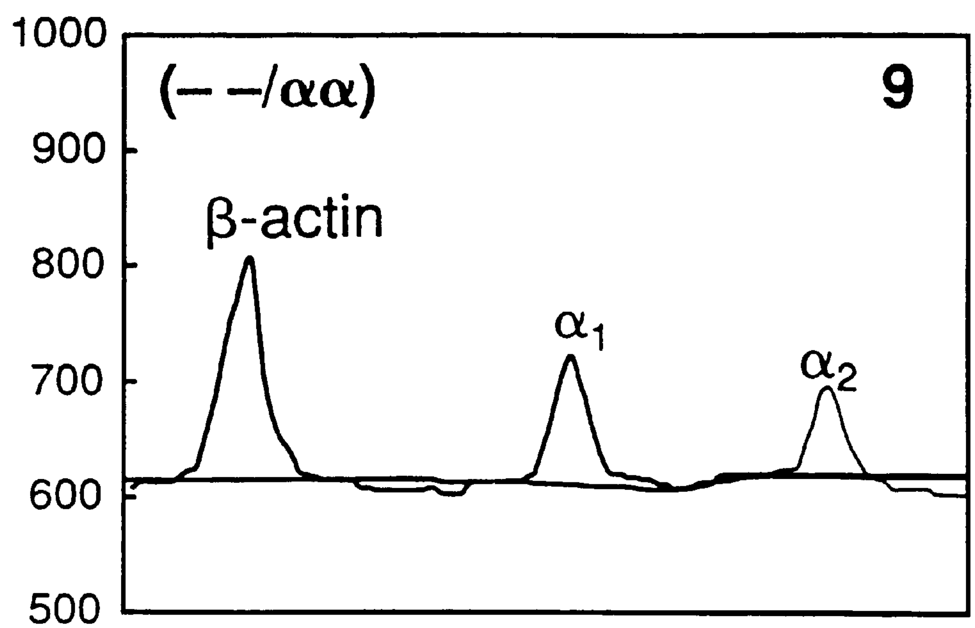
Figure 4D:
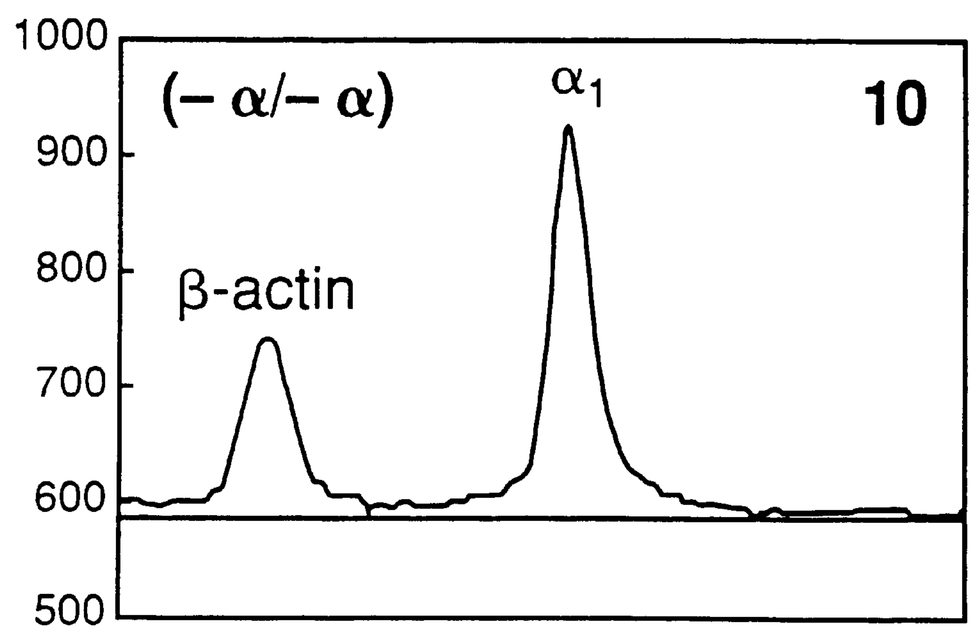
Figure 4E:
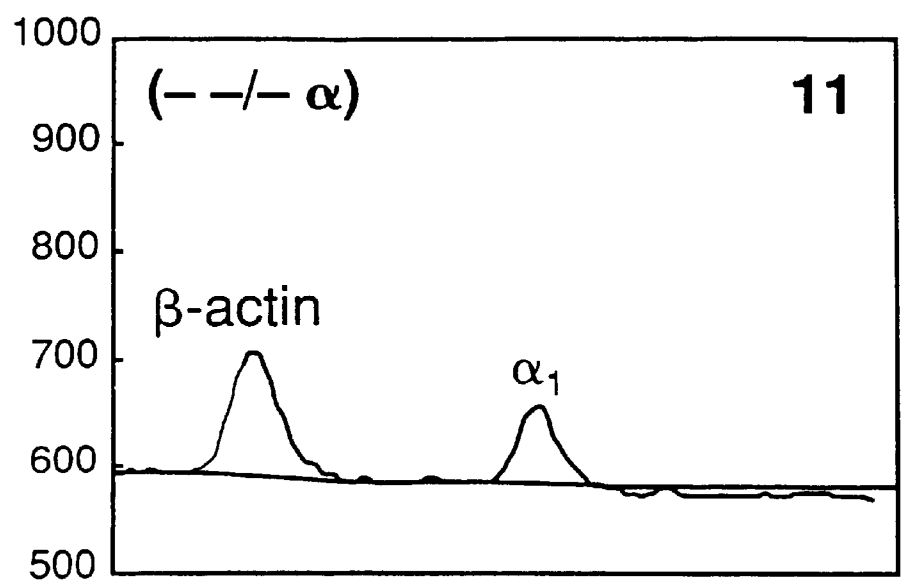
Figure 4F:
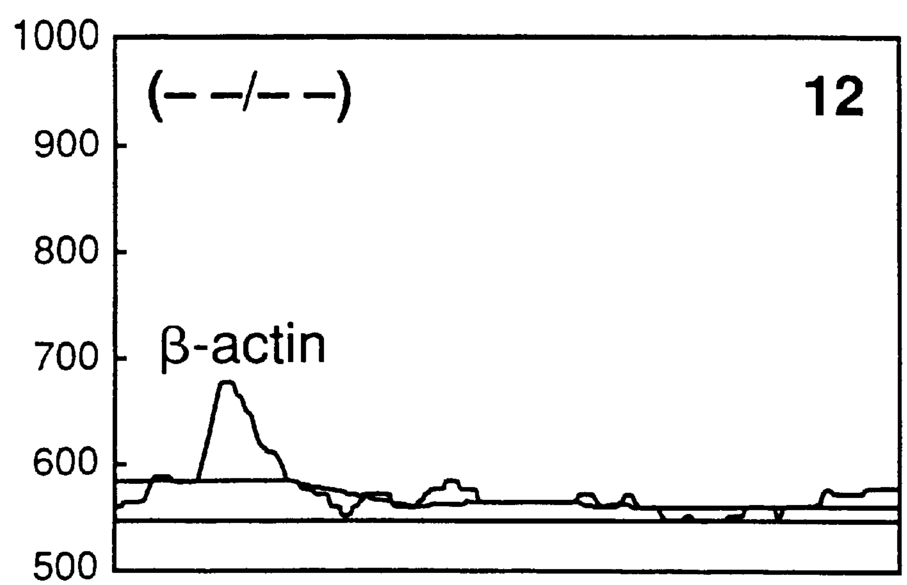

Genomic DNA was isolated from either whole blood or dried blood samples embedded on a filter paper from 21 normal subjects and 62 α-thalassemia patients. This DNA was used as a template to amplify by PCR three DNA fragments ($\alpha_2$, $\alpha_1$ and β-acting genes) which were easily identified from each sample tested. In normal 4 genes (αα/αα) samples, all three bands showed almost equal intensity, which indicated $\alpha_1$ or $\alpha_2$ genes are present normally without any gene deletion (FIG. 3, lanes 1–3). When the intensity of each amplified α gene was compared with the intensity of the β-actin gene band (a gene product which serves as an internal control), deletion of $\alpha_1$ or $\alpha_2$ gene could be identified from ethidium bromide-stained NuSieve agarose gel. Such heterozygotes (–α/αα) possess a mild α-chain deletion resulting from the presence of only three α genes. The band for $\alpha_2$ gene (292 bp) was found to have less intensity (half intensity of normal $\alpha_2$ gene band) as compared to $\alpha_1$ gene (190 bp) FIG. 3, lanes 4–6). α thal-1 Heterozygotes (– –/αα) as well as homozygotes (–α/–α), possessed moderate α-chain deficiency resulting from the presence of only two α-chain genes, in which less intensity of both 190 bp and 292 bp bands (FIG. 3, lanes 10–12) were observed. However Hb H disease (– –/–α) resulted from deletion of three α-gene showed that complete loss of 292 bp band and less intensity of $\alpha_1$ band compared with β-actin band (FIG. 3, lanes 13–15), while the Hb Bart's hydrops fetalis syndrome (– –/– –) had neither $\alpha_2$ nor $\alpha_1$ gene band (FIG. 3, lanes 16–18). Using this set: of PCR primers, different band intensity from each target gene could reflect the genotype status of a gene detection in α-thal patients. A total of 21 normal samples and 62 α-thal patients representing different α gene deletions were examined by this assay.

EXAMPLE 2

Quantitation of PCR-amplified Hemoglobin Alpha Gene Using a Photo-densitometer With Statistical Estimations of Band Intensities In order to obtain quantitative values from this assay, a negative film taken from ethidium bromide stained gel was applied to a densitometer (UltrascanXL enhancer laser densitometer, LKB) to quantitate the area under curve reflecting the intensity of each band. As shown in FIG. 4, different α-gene deletions exhibited different gel scanning patterns of the three peaks (corresponding to β-actin, $\alpha_1$ and $\alpha_2$ bands. The pattern of the peaks correlated very well with the status of α gene deletion, and each genotype has its own characteristic pattern of the peaks. For example, in (–α/αα) an $\alpha_2$ peak is much lower than that of $\alpha_1$ band, while the $\alpha_1$ peak is obviously much higher than that of the β-actin [FIG. 4 (B)]; In (– –/αα), both $\alpha_1$ and $\alpha_2$ peak are lower than that of β-actin [FIG. 4 (C)]; In (–α/–α) the $\alpha_2$ peak diminished, only peaks for $\alpha_1$ and β-actin were observed [FIG. 4 (D)].

The intensity of each band could be represented by the area under the curve. The copy number of a gene then is determined by either the ratio of the area for α gene band to that of β-actin gene, or by comparing the percentage of area from each peak. The average values of ratio and the percentage of peak area are summarized in the Table 1. There are significant differences between each category of the α-thal syndromes.

The ratios of band intensity among $\alpha_1$ over β-actin or $\alpha_2$ over β-actin in normal subject was 1.10±0.25 and 0.70±0.35, respectively, while in α-thal patients with different genotypes a significant change in the calculated values were seen (Table 1). The two clinical significant types of α-thal syndrome, (–α/αα) and (– –/αα) could be identified either comparing the percentage of each band or ratios of $\alpha_1$/β-actin and $\alpha_2$/β-actin.

EXAMPLE 3

Detection of Hemoglobin α Gene by Using DNA-PCR-mediated Color Complementary Assay (CCA) From both Normal and α-thal Patients.

1) Experimental Design

Another quicker (without gel electrophoresis), PCR-mediated color complementary assay (CCA) for detecting a globin gene(s) deletion was developed. It is based on the simultaneous amplification of two α genes with fluorescent-labeled oligonucleotide primers and the visualization of the e-color gene products by UV light irradiation (Chehab and Kan, 1989). Thus, the generation of a color or combination of colors from the patient samples can be visualized under UV light in the tube without electrophoresis. In this CCA, 2 different fluorophores were coupled to B1 or B2 primer in order to detect and differentiate globin gene $\alpha_1$ or $\alpha_2$. In the same PCR mixture B1 or B2 primer that are differently labeled with either fluorescein or rhodamine were added. The primer B1 was labeled with 5'-carbon fluorescein (FAM) appears with a green color, while the B2 primer was labeled with 6-carboxyl-X-rhodamine (ROX) showing red color. The common 5' primer was unlabeled primer A. After coamplification of both $\alpha_1$ and $\alpha_2$ colored-PCR products were produced in the reaction tubes.

2) Optimal Condition for PCR-CCA

The oligonucleotide B1 and B2 with a primary amino group attached to the 5' end were synthesized. The dye-labeled oligonucleotide were then purified from the nonconjugated oligonucleotide by HPLC Aquepore 300C-8 column. The recovered fluorescent oligonucleotide were then dried down and resuspended in sterile distilled water. Measurement of the absorbance of the oligos at 260 nm was performed and diluted to a final concentration of 25 μM. Aliquot of the dye-labeled primers are stored at −20° C. in the dark until use.

PCR mediated CCA reaction was processed as follows: 2 μl of each primer A, FAM-B1 and ROX-B2 was mixed with 1 μg of genomic DNA in a 50 μl reaction mixture containing 5 μl reaction buffer (50 mM KCl, 10 mM Tris (pH8.0), 1.5 mM $MgCl_2$), and 4 μl each dATP, dCTP, dGTP, dTTP at 125 μM. 5 units of native Taq DNA polymerase was added, and the reaction mixture was overlaid with 50 μl of mineral oil. First, amplification reaction is performed at 94° C. for 5 min., 60° C. for 1 min., and 72° C. for 1.0 min. Thirty amplification cycles were followed at 94° C. for 1 min., 60° C. for 1 min., 72° C. for 1 min. Aliquots (10–15 μl) from each amplification mixture were loaded on 6% TBE gel for electrophoresis to confirm the existence and size of amplified product. Also detected were PCR-CCA products by color reactions without electrophoresis. After PCR, amplified samples were separated from free primers by repeated ultrafiltration through Centricon 100 micro concentrators (Amicon). The tubes then were visualized on a long wavelength (300 nm) UV transilluminator and photographed with a Polaroid MP-4 Land Camera. Each film is exposed at f4.5 for 30 sec to 1 min. with a combination of Wratten gelatin filter no.16 and no.21. On the basis of the PCR-CCA data from the large number of samples tested, a range of quantitative values corresponding to normal and the different genotypes of α-thal syndromes can be defined, using a fluorescent spectrophotometer.

3). Detection of Alpha Gene From Normal and α-thal Syndrome Patients by CCA

Figure 5A:
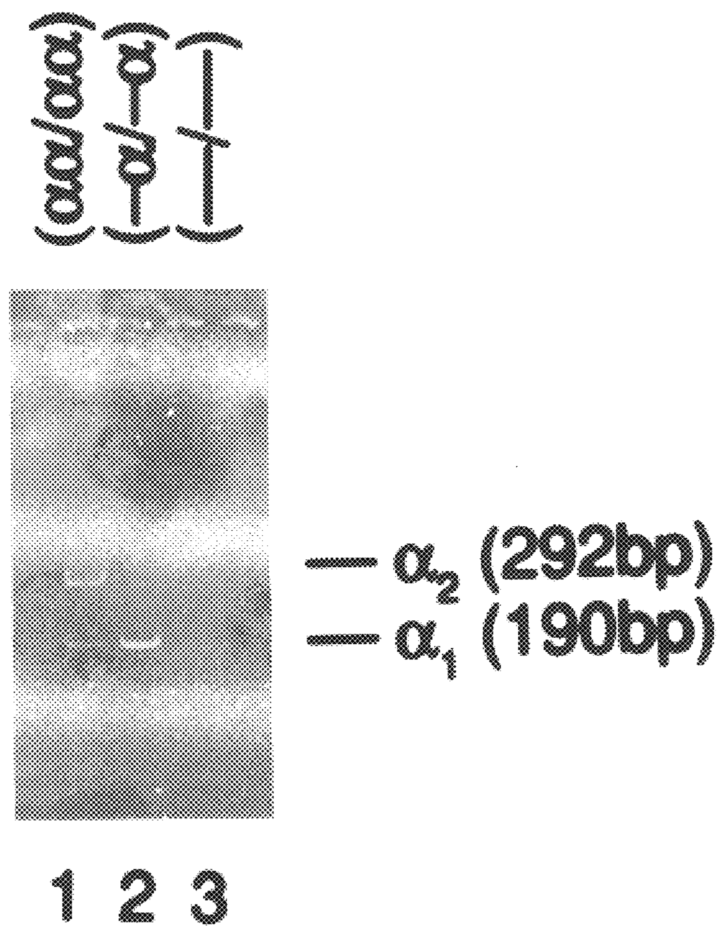
FIG. 5. PCR-mediated CCA from normal and two α-thal syndrome patients. Panel A shows the amplified a genes with different colors in the reaction tubes as viewed with UV-light. In lane 1 is an orange color, the result of an equal mixture of red and green fluorescein dye product amplification; lane 2 displays green due to the absence of red (α2) amplification; lane 3 is colorless due to the total absence of alpha genes (– –/– –) for amplification. Panel B: the amplified αgenes were separated by electrophoresis on a TBE gel and visualized under UV-light by the color and size of each α gene fragment.
Figure 5B:
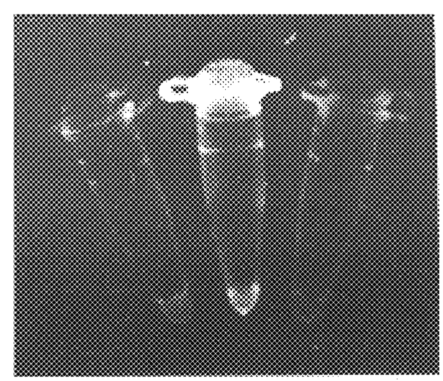

PCR template and reaction conditions were the same as described in Example 1 above. When detection of PCR-CCA a gene in solution was used (directly visualization), amplified products were separated from free primers by ultrafiltration through centricon C 100 microconcentrators after PCR. Colors were observed in the tubes under UV light. As shown in FIG. 5A, both $\alpha_1$ and $\alpha_2$ genes from both normal and several α-thal patients have been successfully amplified. In normal subjects the existence of both $\alpha_1$ and $\alpha_2$ gene produced a color combination (yellow) from $\alpha_1$ gene (green) and $\alpha_2$ gene (red) (FIG. 5. A1). In (−α/−α) patient only α1 gene (green) was observed (FIG. 5.A2), and in (−−/−−) patient, no color were detected (FIG. 5.A3). We also confirmed the bands as specific amplified DNA fragments by visualizing with color photography from the TBE gels (FIG. 5B). Two of each category subjects has been tested in this assay.

REFERENCES

Agrawal et al. (1986) *Nucl. Acid Research* 14:6227–6245.

Bowden O, Vickers M A, Higgs D R. (1992) A PCR-based strategy to detect the common severe determinants of α-thalassemia. *British. Journal. of Hematology* 81:104–108.

Bruening M H, Madan K. Verjall M. Wijnen J T, Meera K P, and Peason P L (1987) Human α globin maps to pter-p13.3 in chromosome 16 distal to PGP. *Human Genetics.* 76,287–289.

Buckel V J, Higgs D R, Wilkie A O M, Super M and Weatheral D J (1988) Localization of human α globin to 16p13.3-pter. *J. of Medical Genetics* 25:847–849

Chehab F F and Kan Y W (1989) Detection of specific DNA sequences by fluorescence amplification: a color complementary assay. *Proc.Natl.Acad.Sci.USA* 86 (23) :9178–9182

Chollet, et al. (1985) *Nucleic Acids Research* 13:1529–1541.

Cong V J, Shong H P (1982) Hydrops fetalis and hemaglobinpathy. *Chinese J. of Obstetrics and Gynecology.* 17:226–228.

Didenko V V; Homsby P J. A quantitative luminescence assay for nonradioactive nucleic acid probes. *J. Histochem Cytochem* 1996 Jun.44(6):657–60.

Higgs D R, Vickers M A, Mikle A O M, Pretorius I M, Jarman A P and Weatherall D J (1989) A review of the molecular genetics of the human α-globin gene cluster. *Blood* 73:1081–1104.

Higgs D and Weatherall D J (1993) *Bailliere's Clinical Hematology* Vol 6 No.1. Bailliere and Tindal press.

Lamture J B; BeattiLe K L; Burke B E; Eggers M D; Ehrlich D J; Fowler R; Hollis M A; Kosicki B B; Reich R K; Smith S R; et al. Direct detection of nucleic acid hybridization on the surface of a chargecoupled device. *Nucleic Acids Res* 1994 Jun.11;22(11):2121–5.

Liang S T, Wong V C W, So W W K, Ma H K, Chan V. Todd D (1985) Homozygous α-thalassemia: clinical presentation. Diagnosis and management. A review of 46 cases. *British Journal of Obstetrics and Gynecology.*92:680–684.

Lie-Injo L E, Hie J B (1960) A fast-moving hemoglobin in hydrops feotalis. *Nature* 185:698.

Mathews et al. (1988) *Anal. Biochem.* 169:1–25.

Weatherall D J and Clegg J (1981) The thalassemia syndromes 3rd ed. Blackwell Scientific Publications. Oxford.

We claim:

1. A nucleic acid composition comprising a nucleic acid consisting of SEQ ID NO: 1, a nucleic acid consisting of SEQ ID NO: 2, and a nucleic acid consisting of SEQ ID NO: 3.

2. A method for detecting a form of α-thalassemia in a biological sample containing nucleic acids encoding hemoglobin comprising:

(a) forming a mixture comprising primers and said biological sample, wherein said primers include a primer consisting of SEQ ID NO: 1 that specifically hybridizes to a region common to $\alpha_1$ and $\alpha_2$ hemoglobin genes, a primer consisting of SEQ ID NO: 2 that specifically hybridizes to the $\alpha_1$ hemoglobin gene, and a primer consisting of SEQ ID NO: 3 that specifically hybridizes to the $\alpha_2$ hemoglobin gene;

(b) hybridizing said primers to nucleic acids in said biological sample;

(c) extending the 3' ends of the primers to form an $\alpha_1$ extension product and an $\alpha_2$ extension product having different nucleotide lengths;

(d) repeating steps (b) and (c), thereby amplifying said $\alpha_1$ and $\alpha_2$ extension products; and (e) detecting amplified extension products of (d), wherein absence of an $\alpha_1$ amplified extension product and/or an $\alpha_2$ amplified extension product is indicative of the presence of a form of $\alpha$-thalassemia.

3. A method for detecting a form of $\alpha$-thalassemia in a biological sample containing nucleic acids encoding hemoglobin comprising:

(a) forming a mixture comprising primers and said biological sample, wherein said primers include a primer consisting of SEQ ID NO: 1 that specifically hybridizes to a region common to $\alpha_1$ and $\alpha_2$ hemoglobin genes, a primer consisting of SEQ ID NO: 2 that specifically hybridizes to the $\alpha_1$ hemoglobin gene, a primer consisting of SEQ ID NO: 3 that specifically hybridizes to the $\alpha_2$ hemoglobin gene, and primers that specifically hybridize to nucleic acids encoding an internal standard;

(b) hybridizing said primers to nucleic acids in said biological sample;

(c) extending the 3' ends of the primers to form an $\alpha_1$ extension product and an $\alpha_2$ extension product having different nucleotide lengths, and an internal standard extension product;

(d) repeating steps (b) and (c), thereby amplifying said $\alpha_1$ and $\alpha_2$ extension products and said internal standard extension product; and (e) detecting amplified extension products of (d), wherein absence of an $\alpha_1$ amplified extension product and/or an $\alpha_2$ amplified extension product, or a lesser amount of $\alpha_1$ amplified extension product and/or an $\alpha_2$ amplified extension product as compared to internal standard amplified extension product, is indicative of the presence of a form of $\alpha$-thalassemia.

4. The method of claim 2 or claim 3, wherein the biological sample comprises a dried blood sample.

5. The method of claim 2 or claim 3, wherein said amplified extension products are separated prior to detection.

6. The method of claim 5, wherein separation is by electrophoresis.

7. The method of claim 2 or claim 3, wherein the primer consisting of SEQ ID NO: 2 and the primer consisting of SEQ ID NO: 3 are labeled.

8. The method of claim 7, wherein each of said primers of (a) is labeled.

9. The method of claim 8, wherein each of said primers of (a) is labeled with a different label.

* * * * *

SEQUENCE LISTING

```
(1) GENERAL INFORMATION:

   (iii) NUMBER OF SEQUENCES:  3


(2) INFORMATION FOR SEQ ID NO:1:

     (i) SEQUENCE CHARACTERISTICS:
          (A) LENGTH:  23
          (B) TYPE:  NUCLEIC ACID
          (C) STRANDEDNESS:  UNKNOWN
          (D) TOPOLOGY:  UNKNOWN

    (ii) MOLECULE TYPE:
          (A) DESCRIPTION: OLIGONUCLEOTIDE

    (ix) FEATURE:
          (A) NAME/KEY: A PRIMER
          (D) OTHER INFORMATION: 5' PRIMER COMMON TO
               BOTH ALPHA-1 AND ALPHA-2 GENES.

    (xi) SEQUENCE DESCRIPTION: SEQ ID NO:1:

TGACCCTCTT CTCTGCACAG CTC                                          23


(2) INFORMATION FOR SEQ ID NO:2:

     (i) SEQUENCE CHARACTERISTICS:
          (A) LENGTH:  21
          (B) TYPE:  NUCLEIC ACID
          (C) STRANDEDNESS:  UNKNOWN
          (D) TOPOLOGY:  UNKNOWN

    (ii) MOLECULE TYPE:
          (A) DESCRIPTION: OLIGONUCLEOTIDE

    (ix) FEATURE:
          (A) NAME/KEY: B1 PRIMER
          (D) OTHER INFORMATION: CORRESPONDS TO A
               REGION OF THE 3' UNTRANSLATED PORTION OF
               THE ALPHA-1 GENE.

    (xi) SEQUENCE DESCRIPTION: SEQ ID NO:2:

GAGGCCCAAG GGGCAAGAAG C                                            21


(2) INFORMATION FOR SEQ ID NO:3:

     (i) SEQUENCE CHARACTERISTICS:
          (A) LENGTH:  23
          (B) TYPE:  NUCLEIC ACID
          (C) STRANDEDNESS:  UNKNOWN
          (D) TOPOLOGY:  UNKNOWN

    (ii) MOLECULE TYPE:
          (A) DESCRIPTION: OLIGONUCLEOTIDE

    (ix) FEATURE:
          (A) NAME/KEY: B2 PRIMER
          (D) OTHER INFORMATION: CORRESPONDS TO A
               REGION OF THE 3' UNTRANSLATED PORTION OF
               THE ALPHA-2 GENE.

    (xi) SEQUENCE DESCRIPTION: SEQ ID NO:3:

TTCCGGGACA GAGAGAACCC AGG                                          23
```